United States Patent
Castellana

(10) Patent No.: US 10,874,883 B2
(45) Date of Patent: Dec. 29, 2020

(54) PRODUCT FOR TREATING THE SKIN AND MUCOUS MEMBRANES, AND RELATIVE METHOD OF PREPARATION

(76) Inventor: Rossana Castellana, Trieste (IT)

(*) Notice: Subject to any disclaimer, the term of this patent is extended or adjusted under 35 U.S.C. 154(b) by 370 days.

(21) Appl. No.: 12/086,453

(22) PCT Filed: Dec. 12, 2006

(86) PCT No.: PCT/IB2006/003558
§ 371 (c)(1),
(2), (4) Date: Jun. 12, 2008

(87) PCT Pub. No.: WO2007/069024
PCT Pub. Date: Jun. 21, 2007

(65) Prior Publication Data
US 2009/0110646 A1    Apr. 30, 2009

(30) Foreign Application Priority Data
Dec. 13, 2005   (IT) .............................. UD2005A0211

(51) Int. Cl.
| A61K 9/12 | (2006.01) |
| A61K 33/40 | (2006.01) |
| A61P 31/00 | (2006.01) |
| A61Q 19/00 | (2006.01) |
| A61K 8/36 | (2006.01) |
| A61K 8/22 | (2006.01) |
| A61K 31/19 | (2006.01) |

(52) U.S. Cl.
CPC ................ *A61Q 19/00* (2013.01); *A61K 8/22* (2013.01); *A61K 8/36* (2013.01); *A61K 31/19* (2013.01); *A61K 2800/28* (2013.01); *A61K 2800/52* (2013.01)

(58) Field of Classification Search
CPC . A61K 8/22; A61K 8/36; A61K 31/19; A61K 2800/28; A61K 2800/52; A61P 17/00; A61P 17/16; A61P 17/18; A61P 17/10; A61P 31/00; A61Q 19/00
See application file for complete search history.

(56) References Cited

U.S. PATENT DOCUMENTS

| 3,686,289 A | 8/1972 | Fletcher et al. |
| 4,874,361 A | 10/1989 | Obaji |
| 5,166,176 A | 11/1992 | Obagi et al. |
| 5,259,888 A * | 11/1993 | McCoy ..................... C11D 3/30 134/2 |
| 5,560,857 A * | 10/1996 | Sakon ............... H01L 21/02052 134/3 |
| 5,827,884 A | 10/1998 | Obagi et al. |
| 7,465,408 B1 * | 12/2008 | Avanzino ................ C23C 22/52 216/100 |
| 2004/0101571 A1 | 5/2004 | Reed et al. |
| 2004/0109872 A1 * | 6/2004 | Villani ..................... 424/195.16 |
| 2005/0010161 A1 * | 1/2005 | Sun et al. ......................... 604/20 |
| 2005/0163933 A1 * | 7/2005 | Dietsche ................ B05D 7/142 427/384 |
| 2006/0188554 A1 * | 8/2006 | Nakashima et al. .......... 424/448 |

FOREIGN PATENT DOCUMENTS

| EP | 0700897 A1 | 3/1995 |
| JP | 7-283192 | 10/1995 |
| JP | A-0728192 | * 10/1995 ........... H01L 21/304 |
| JP | 10 513 452 | 12/1998 |
| JP | 2005-281133 | * 10/2005 ............... A61K 7/00 |
| JP | 2005 281133 A | 10/2005 |
| JP | 2005281133 | 10/2005 |
| WO | WO 96/23490 | 8/1996 |
| WO | WO 02/072018 A | 9/2002 |
| WO | WO 02/072018 A2 | 9/2002 |
| WO | WO 2005/011683 A1 * | 2/2005 ......... A61K 31/4174 |

OTHER PUBLICATIONS

Buffer Solution: retrieved from internet: http://en.wikipedia.org/wiki/Buffer_solution.retrieved on Nov. 14, 2013.*
Gel: retrieved from internet: http://pskills.pharm.ku.edu/ios/html5/html5-compoundingvideos/html5-revised-lecture-video/Gels/Gels.pdf. Retrieved on May 25, 2016.*
Glycerine: retrieved from internet: https://www.aciscience.org/docs/Glycerine_-_an_overview.pdf. retrieved on May 23, 2018.*
Schmucker, J. et al., "Rheology Modification of Hydrogen Peroxide-Based Applications Using Cross-Linked Polyacrylic Acid Polymers" *International Journal of Cosmetic Science*, 1999, 21, 313-325.
Notice of Reasons for Rejection, Jul. 4, 2012, received in Japanese counterpart application JP 2008-545126 (Both in Original Japanese and in English language translation).

* cited by examiner

*Primary Examiner* — Hong Yu

(57) ABSTRACT

A method for preparing a product for treating the skin and mucous membranes comprises the steps of making available a suitable quantity of trichloroacetic acid, making available a suitable quantity of hydrogen peroxide, making a first mixture of the trichloroacetic acid and the hydrogen peroxide, making available a determinate quantity of the basic compound able to achieve a buffer effect of the trichloroacetic acid comprised in the first mixture, and adding the basic compound.

16 Claims, No Drawings

PRODUCT FOR TREATING THE SKIN AND MUCOUS MEMBRANES, AND RELATIVE METHOD OF PREPARATION

BACKGROUND OF THE INVENTION

Field of the Invention

The present invention concerns a product for treating the skin or the mucous membranes, in the medical, aesthetic and/or cosmetic field, and the relative method of preparation.

In particular, the present invention concerns a product and the relative method to produce it, to be used in the treatment of problems of the skin and the mucous membranes, such as acne, sun damage, sun freckles, pre-cancerous lesions, problems of pigmentation, damage deriving from episodes of scarring, both due to wounds and also to the effects of pathologies, atrophy, hypertrophy, retraction and alteration of the scarring of every part of the body, including the gums, damage caused by ageing, such as wrinkles, sagging of the skin and suchlike.

Here and in the rest of the description, by mucous membrane we mean a membrane that covers the inner face of some organs, such as the vesical mucous, the mucous of the nose and of the intestine, the inner region of the mouth, including the gums, and which is kept continuously moist by the secretion of muciferous glands or of other type of glands. It consists of an epithelium, facing towards the free surface, and an underlying layer of connective tissue, possibly containing muscular fibers and lymphocytes.

Description of Related Art

In medical and aesthetic/cosmetic routines, the practice of chemical peeling in the surgery is known, to treat skin problems by means of the direct application on the region of damaged skin of various chemical substances such as trichloroacetic acid (TCA), in various concentrations, according to the desired and necessary depth of the intervention, which goes from the epidermis to the dermis.

The skin, as is known, is divided into two parts: the inner dermis, which mainly contains blood vessels, nerve ends, fibroblastic cells for the biosynthesis of elastin and collagen, immersed in an amorphous substance rich in glycosoaminoglycans, called "fundamental substance"; and the outer epidermis, further divided into the Malpighian layer, formed by a living tissue divided again into basal, spinous and granular, and the corneous layer, formed by a dead tissue, which is the layer visible to the naked eye.

In particular, the known indications regarding treatment with TCA concern both medical affections such as widespread actinic damage with contiguous actinic keratosis, that is, the circumscribed proliferation of the corneous layer of the epidermis; they also concern aesthetic conditions such as the ageing of the face and sun freckles.

The more concentrated the TCA, the more it penetrates in depth into the epidermis and the dermis, and consequently the stronger its denaturing effect on the layers of the dermis and epidermis. The depth of the desired tissue necrosis is therefore correlated to the concentration of the TCA.

For example, a solution comprising TCA in a concentration of less than 25% w/w entails the exfoliation of the epidermis, whereas a solution comprising TCA at about 30-40% w/w causes dermal necrosis of 0.3-0.5 mm, the depth normally required to renew skin with actinic damage. The in-depth penetration of TCA, to the level of the papillary dermis, is fundamental for renewing the tissue of the epidermis and dermis and is signaled by the start of a subcutaneous edema in the region treated, associated with a whitening of the skin, due to the denaturing of the skin proteins.

Moreover, from a histological point of view, the effects of medium-depth chemical peeling with TCA are, among others: improvement of sun elastosis and replacement with thick and homogenized bands of dermal collagen, that is, neo-collagenogenesis, with cytological and architectural normalization of the epidermis.

However, TCA is an extremely aggressive agent which, when it is very concentrated, on the one hand brings the benefits of exfoliation and renovation of the epidermis, and on the other hand, in order to obtain these benefits, has serious side effects, since the TCA itself must inevitably penetrate in depth, passing through the epidermis as far as the dermis, and thus causing structural damage to the epidermis and the dermis, due to the effect of the hydrogen ions of the TCA which cause denaturation and precipitation of the epidermal proteins, giving rise to the known visual effect of whitening of the surface skin, also known as "white frost". The denaturation of the proteins produces an eschar, that is, a plaque of altered tissue which forms in association with a necrotizing process of the skin; curing this will give as a result the desired skin renewal; however, this happens over 7-10 days, during which interval the skin of the patient's face is covered by a thick "crust" of a brown and/or grayish color, clearly impeding the patient normal social life.

One purpose of the present invention is to produce a product for treating the skin and the mucous membranes, based on TCA, which allows a tissue renewal due to the TCA, but without damaging the surface layers of the epidermis.

Another purpose is to perfect a method to produce said product for treating the skin and the mucous membranes.

The Applicant has devised, tested and embodied the present invention to overcome the shortcomings of the state of the art and to obtain these and other purposes and advantages.

BRIEF SUMMARY OF THE INVENTION

The present invention is set forth and characterized in the main claim, while the dependent claims describe other characteristics of the invention or variants to the main inventive idea.

In accordance with the above purposes, a product for treating the skin and the mucous membranes according to the present invention can be obtained by means of a method that comprises the following steps:

a) to make available a suitable quantity of trichloroacetic acid ($CCl_3COOH$ or TCA);

b) to make available a suitable quantity of hydrogen peroxide ($H_2O_2$);

c) to make a first mixture of said trichloroacetic acid of step a) with said hydrogen peroxide of step b);

d) to make available a determinate quantity of basic compound, able to achieve a buffer of said first mixture comprising said trichloroacetic acid;

e) to add, to said first mixture, said basic compound of step d) in order to buffer, that is, to fix the value of pH of said first mixture comprising said trichloroacetic acid at a desired value.

DETAILED DESCRIPTION OF THE INVENTION

According to the present invention, the pH of the product, obtained by means of the described buffer effect of the first mixture, is comprised between about 2.3 and 2.6. According to a preferential form of embodiment, the pH of the product is about 2.5. According to an advantageous feature of the present invention, the above basic compound used is at least a compound chosen from a group comprising ammonia ($NH_3$), triethanolamine and suchlike, or mixtures thereof. Advantageously, the basic compound is used in stoichiometric quantity, or in excess, according to requirements, in order to achieve a buffer effect of the first mixture comprising the trichloracetic acid: According to an advantageous form of embodiment of the present invention, the basic compound is ammonia, suitable to diminish the aggressiveness of the TCA. Advantageously, the use of ammonia or triethanolamine prevents the risk of evolution of toxic metabolites from the buffer reaction of the trichloracetic acid. According to the present invention, the production of the first mixture in step c) involves a reaction of an endothermic type.

According to the present invention, furthermore, step e), using in this case ammonia, involves an exothermic reaction, which reaches in this case a temperature of about 50° C. According to the present invention, in order to provide an effective product the reaction must be carried out at a controlled temperature and greater than ambient temperature. Advantageously, the reaction is controlled by cooling means, of a known type, which limit the increase in temperature to about 40-45° C.; in this way, the final product surprisingly has greater efficaciousness in its use for pathologies and aesthetic problems of the skin. According to an advantageous feature of the present invention, the TCA of step a) is supplied substantially pure, except for a minimum quantity of humidity due to the high hygroscopicity of the TCA itself, for example in the form of crystals, usually very deliquescent. According to another form of embodiment of the present invention, the TCA in step a) can be obtained, on the contrary, starting from precursors of the TCA itself, that is, by means of a step of chlorination of acetic acid or chloracetic acid, in the presence of visible light, UV rays or a suitable catalyst. According to the present invention, the TCA of step a) is mixed with hydrogen peroxide to give said first mixture. The first mixture comprises TCA, said TCA having a concentration comprised in a range of between about 15 and 50%, preferably between 25 and 40% w/w, even more preferably between 30 and 35% w/w.

According to a preferred form of embodiment of the present invention, the TCA in said first mixture is in a concentration of about 33% w/w; advantageously in this case there is an optimum compromise between the TCA's typical characteristics of exfoliating the skin and its capacity for stimulating the dermis in order to renovate the tissues. According to the present invention, moreover, the hydrogen peroxide is mixed to the TCA in step b), so that the composition of hydrogen peroxide in the first mixture is present to a concentration comprised between about 85 and 50% w/w, preferably between about 75 and 60% w/w, even more preferably between about 70 and 65% w/w. According to a preferred form of embodiment of the present invention, the composition of hydrogen peroxide in the first mixture is about 67% w/w. According to an advantageous form of embodiment of the product, after step e) a gelling step is performed in which a thickening agent is added, for example silica based, such as AEROSIL® 200 Pharma, advantageously resistant to the pH values obtained, or Sepigel (Seppic) or others, to make the product spreadable; it is also possible to add glycerin, to improve the compatibility of the product and absorption into the skin.

The final product, after the gelling step, has a pH value, measured with a standard method that provides to dilute the sample, even greater than the starting pH comprised between about 2.3 and 2.6, for example comprised between about 5 and 6.

According to another form of embodiment of the invention, the final product may not comprise trichloroacetic acid but may comprise the relative reaction products.

Advantageously, the product according to the present invention has good characteristics of renewing the tissues of the epidermis and dermis.

Advantageously, by applying the product according to the present invention, the effect of in-depth renewal, on the level of the papillary dermis, is shown by the onset of an evident edema under the skin, but without the corresponding whitening of the region affected, that is, without any denaturation of the epidermis proteins occurring.

Applicant has also developed a method for the application of the product according to the present invention, on damaged skin; according to the method of application, the product is applied by means of direct and prolonged massage on the skin, or by means of applications with a brush and suchlike.

In this case, the onset of the sub-cutaneous edema and the modification of coloring due to vasoconstriction can be seen. This modification is indicative of the fact that the TCA has reached the level of the dermis papillae and therefore there follows a stimulation and renewal of the dermis, with an increase of the neo-collagenogenesis, but without altering or damaging the surface of the skin.

Applicant has hypothesized an action mechanism of the product according to the present invention, connected to the different speed and depth of penetration of the hydrogen peroxide and the TCA or the relative reaction products. In fact, the hydrogen peroxide has high tropism and rapidly enters into the skin cells, but substantially only into the surface skin cells. On the contrary, the hydrogen ions H+ of the TCA or the relative reaction products enter more slowly into the skin, but also more deeply into the epidermis and the dermis; when they arrive in the surface skin cells, they are at least partly inactive on a surface level, or buffered, preventing any aggressive and harmful action on the epidermis, while on a deeper level the quantity of TCA that penetrates is able to perform its activity of irritation and vasoconstriction, which stimulates the repair and hence cell renewal and neo-collagenogenesis. Advantageously, the TCA and the hydrogen peroxide are not toxic for the organism. According to another advantageous feature, the product according to the present invention is comprised in a preparation, such as a cream, an ointment, a liquid, a gel, an aerosol and suchlike, which can be administered or applied locally or can be directed directly onto the damaged region of the patient's skin. Therefore, the use of the product according to the present invention has been applied experimentally to cosmetic/aesthetic treatments on the skin, and medical treatments of skin pathologies. In particular, Applicant has successfully treated the pathology of acne. In this case, juvenile acne and the scars resulting from acne have been experimentally treated, both successfully and without side effects. In fact, advantageously, the action against the effects of acne occurs both in a surface action of an exfoliating type, which frees the outlet ducts, and also in an in-depth action in the pustules, penetrating deeply and acting selectively on the inflamed sebaceous follicle in order to stimulate repair of the pustules without scarring. Apart from preventing scarring after active acne, the product according to the present invention adds a surprising anti-septic action on the local bacterial flora, due to the synergic effect of the TCA and the hydrogen peroxide. Advantageously, the results were unexpectedly positive with patients under treatment with isotretinoin, because generally isotretinoin is a drug which, giving alterations to the cicatrisation of the lesions, counter-indicates any other ablative peeling. In general, there was also an advantageous improvement in the compliance of the patient and an improvement in the results of the therapies. Surprisingly, moreover, the repeated medical application of the product according to the present invention impedes and contrasts the onset of scars. According to the present invention, Applicant also used the product experimentally for the treatment of recent depressed scars, such as for example resulting from pathologies such as chicken pox, with considerable results in recovering connected scars. According to another feature of the present invention, Applicant experimentally and successfully used the product according to the present invention for the treatment of unwanted dermal-epidermal pigmentations, such as chloasma or hyper-pigmentary reactivity in high phototypes, without any side effects, whereas traditional peeling, by causing inflammation, can aggravate such aesthetic problems. Advantageously, an even better result was noted with the use of the present invention in association with tyrosinase inhibitors in home treatments, since it promotes penetration. According to another characteristic feature, Applicant successfully used the product according to the present invention experimentally for the treatment of photo-ageing of the skin. In this case, the effect of stimulating the dermis was positive, with an optimum result in improving the skin texture, the coloring and luminosity of the skin and a drastic reduction of dilated pores. Furthermore, in the case of photo-ageing of the skin, the present invention gave a surprising improvement in skin tone, shown immediately by the onset of the edema, which persisted over months with the repetition of the application in subsequent sittings for treating neo-collagenogenesis. Advantageously, moreover, an improvement was found in the result and duration of the re-absorbable fillers, such as for example collagen, polylactic acid, hyaluronic acid, since it increases compactness of the dermis and prevents these materials from being dispersed. Furthermore, Applicant has also treated, experimentally and with positive results, the pathology of drooping breasts, since the firming up of the skin stimulates a greater swelling of the gland. Advantageously, moreover, the present invention can be used in the field of dentistry, thanks to the combined anti-septic and renovating action due to neo-collagenogenesis.

It is clear that modifications and/or additions of parts and/or steps may be made to the product for the skin and mucous membranes and method as described heretofore, without departing from the scope of the present invention.

It is also clear that, although the present invention has been described with reference to some specific examples, a person of skill in the art shall certainly be able to achieve many other equivalent forms of product for the skin and mucous membranes and relative method, having the characteristics as set forth in the claims and hence all coming within the field of protection defined thereby.

I claim:

1. A product for treating the skin and mucous membranes selected from a cream, an ointment, a liquid, a gel, and an aerosol, wherein the product is prepared by:

mixing a suitable quantity of trichloroacetic acid with a composition of hydrogen peroxide ($11_20_2$) to form a first mixture, wherein the trichloroacetic acid in the first mixture is in a concentration of 30% to 35% w/w and the composition of hydrogen peroxide in the first mixture is present in a concentration of about 50% to about 85% providing a determinate quantity of basic compound to buffer the first mixture to obtain a pH value of between 2.3 and 2.6 of the first mixture; and adding the basic compound to the first mixture in order to buffer the first mixture, wherein the buffered first mixture is a product.

2. The product of claim 1, wherein the basic compound is a compound chosen from the group consisting of ammonia, triethanolamine, and mixtures thereof.

3. The product of claim 1, wherein the trichloroacetic acid is supplied substantially pure.

4. The product of claim 1, wherein the trichloroacetic acid is obtained by means of the chlorination of acetic acid, chloroacetic acid or a mixture thereof.

5. The product of claim 1, wherein the trichloroacetic acid in the first mixture is in a concentration of about 33% w/w.

6. The product of claim 1, wherein the product further contains a gelling agent.

7. The product of claim 1, wherein the product further includes a thickening agent.

8. The product of claim 1, wherein the product further includes glycerin.

9. A product for treating the skin and mucous membranes selected from a cream, an ointment, a liquid, a gel, and an aerosol, wherein the product is prepared by:

mixing a suitable quantity of trichloroacetic acid with a composition of hydrogen peroxide ($H_2O_2$) to form a first mixture, wherein the trichloroacetic acid in the first mixture is in a concentration of 30% to 35% w/w and the composition of hydrogen peroxide in the first mixture is present in a concentration of about 50% to about 85% providing a determinate quantity of basic compound that is able to achieve a buffer effect of the trichloroacetic acid comprised in the first mixture; and adding the basic compound to the first mixture in order to buffer the first mixture, wherein the buffered first mixture is a product.

10. The product of claim 9, wherein the basic compound is a compound chosen from the group consisting of ammonia, triethanolamine, and mixtures thereof.

11. The product of claim 9, wherein the trichloroacetic acid is supplied substantially pure.

12. The product of claim 9, wherein the trichloroacetic acid is obtained by means of the chlorination of acetic acid, chloroacetic acid or a mixture thereof.

13. The product of claim 9, wherein the trichloroacetic acid in the first mixture is in a concentration of about 33% w/w.

14. The product of claim 9, wherein the product further contains a gelling agent.

15. The product of claim 9, wherein the product further includes a thickening agent.

16. The product of claim 9, wherein the product further includes glycerin.

* * * * *